United States Patent [19]

Lafon

[11] Patent Number: 4,714,699
[45] Date of Patent: Dec. 22, 1987

[54] 2-TOLYLMORPHOLINE DERIVATIVES AND PHARMACEUTICAL COMPOSITIONS

[75] Inventor: Louis Lafon, Paris, France

[73] Assignee: Societe Anonyme Dite: Laboratoire L. Lafon, Maisons Alfort, France

[21] Appl. No.: 27,350

[22] Filed: Mar. 18, 1987

Related U.S. Application Data

[63] Continuation of Ser. No. 660,219, Oct. 12, 1984, abandoned.

[30] Foreign Application Priority Data

Oct. 14, 1983 [FR] France ................... 83 16406

[51] Int. Cl.$^4$ ................... A61K 31/535; C07D 295/02
[52] U.S. Cl. ................... 514/227; 544/178; 544/173
[58] Field of Search ................... 544/178; 514/227

[56] References Cited

PUBLICATIONS

Busch et al. *Chemical Abstracts,* vol. 86, (1977), No. 5381k.
Lafon, *European Patent Application,* No. 80,940 (6–1983).

*Primary Examiner*—Robert W. Ramsuer
*Attorney, Agent, or Firm*—Wegner & Bretschneider

[57] ABSTRACT

The present invention relates to new 2-tolylmorpholine derivatives, namely, more precisely, (a) 2-p-tolyl-4-isopropylmorpholine and its addition salts,
(b) 2-m-tolyl-4-methylmorpholine and its addition salts,
(c) 2-p-tolyl-4-methylmorpholine and its addition salts,
(d) 2-o-tolyl-4-tert.-butylmorpholine and its addition salts,
(e) 2-p-tolyl-4-tert.-butylmorpholine and its addition salts, and
(f) 2-(m-trifluoromethylphenyl)-2-hydroxy-4-ethylmorpholine and its addition salts.

These new derivatives are useful in therapy, especially as agents active on the CNS.

7 Claims, No Drawings

2-TOLYLMORPHOLINE DERIVATIVES AND PHARMACEUTICAL COMPOSITIONS

This application is a continuation of Ser. No. 660,219, filed Oct. 12, 1984 now abandoned.

The present invention relates to new industrial products belonging to the family of the 2-phenylmorpholine derivatives, namely the 2-tolylmorpholine derivatives described below. It also relates to the use of these new products in therapy, especially as agents active on the central nervous system (CNS).

It is known that a number of compounds belonging to the family of the 2-phenylmorpholine derivatives have already been described and their pharmacological properties studied ; cf., in this connection, No. GB-A-851,311, U.S. Pat. No. 2,835,669, U.S. Pat. No. 2,997,469, No. FR-A-7,443 M, No. FR-A-1,535,615, No. FR-A-2,111,882, No. FR-A-2,471,378, No. EP-A-80,940 and the article by N. BUSCH et al., Eur. J. Med. Chem. Chimica Therapeutica 11 (No.3), pages 201–207 (1976), where the said 2-phenylmorpholine derivatives are proposed or envisaged as excitants, stimulants, tranquillizers, sedatives, anti-inflammatory agents, analgesics and/or hypotensive.

It has just been found, surprisingly, that the compounds according to the invention, which all have sedative effects, are particularly valuable in therapy as sedative and CNS-stimulant substances on the one hand and/or vasodilating substances on the other, having regard to the teaching of the prior art mentioned above. In particular, the compounds according to the invention are more valuable than the 2-o-tolyl-4-methylmorpholine described in No. EF-A-80,940 mentioned above. Furthermore, the compounds according to the invention are not teratogenic, in contrast to certain 2-phenylmorpholine derivatives known in the prior art.

The new 2-tolylmorpholine derivatives according to the invention, which correspond to the general formula

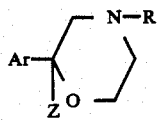

(in which Ar is a tolyl or trifluoromethylphenyl group, Z is H or OH and R is a $C_1$–$C_4$ alkyl group), are selected from the group of 2-tolyl-4-alkylmorpholines consisting of:

(a) 2-p-tolyl-4-isopropylmorpholine and its addition salts,
(b) 2-m-tolyl-4-methylmorpholine and its addition salts,
(c) 2-p-tolyl-4-methylmorpholine and its addition salts,
(d) 2-o-tolyl-4-tert.-butylmorpholine and its addition salts,
(e) 2-p-tolyl-4-tert.-butylmorpholine and its addition salts, and
(f) 2-(m-trifluoromethylphenyl)-2-hydroxy-4-ethylmorpholine and its addition salts.

The expression "addition salts" is understood here as meaning firstly the acid addition salts obtained by reacting the free bases according to the invention with inorganic and organic acids, and secondly the ammonium salts. Hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular among the acids which can be used to salify the free bases according to the invention. $CH_3I$ and $CH_3Cl$ may be mentioned in particular among the compounds making it possible to obtain ammonium salts.

The acid addition salts are preferred to the ammonium salts. The hydrochlorides, which are given in Table I below without implying a limitation, are currently the most valuable of the acid addition salts from the neuropsychopharmacological point of view.

The compounds according to the invention can be prepared in accordance with a method known per se, by the application of classical reaction mechanisms. The method recommended here for the preparation of the compounds in which Z=H consists in cyclizing a 2-(N-alkyl-N-β-hydroxyethyl)amino-1-tolylethanol of the formula

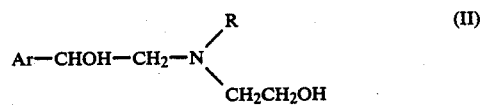

(in which Ar and R are defined as above) by means of concentrated $H_2SO_4$, at a temperature of between 0° and 25° C., for at least 1 hour.

This cyclization is advantageously carried out with concentrated sulfuric acid having a density of 1.84.

The total synthesis of the compounds according to the invention in which Z is H, from a methylphenacyl bromide of the formula III and an N-β-hydroxyethylalkylamine IV, is represented schematically in Diagram A below.

DIAGRAM A

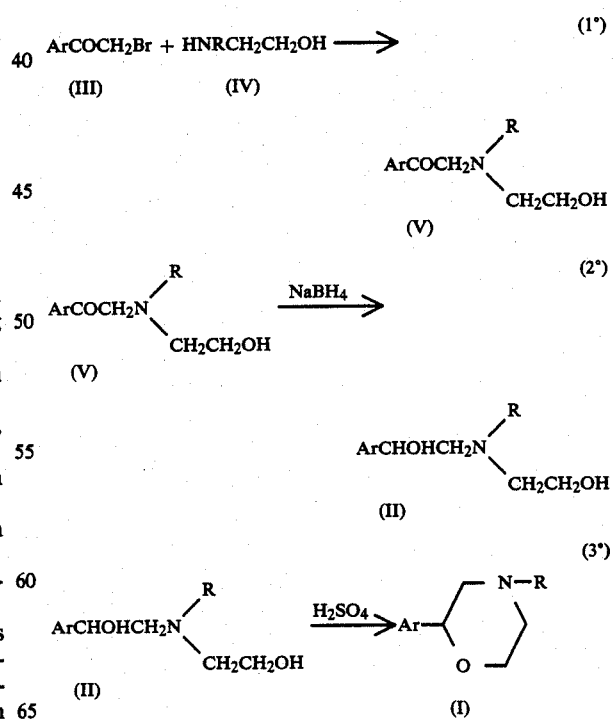

The method recommended here for the preparation of the compound according to the invention in which Z=OH consists in reacting α-bromo-m-trifluoromethylacetophenone (alternative nomenclature: m-trifluoromethylphenacyl bromide) of the formula

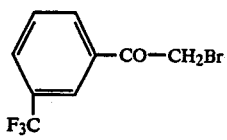
(III bis)

with an excess, relative to the stoichiometric conditions, of the N-β-hydroxyethylalkylamine IV (in which R is ethyl), in an inert solvent, especially dimethyl or diethyl ether. About 2 mol of III bis will advantageously be used per mol of IV, the reaction time being between 4 and 24 hours and the temperature being between 5° and 25° C.

According to the invention, a therapeutic composition is recommended which contains, in association with a physiologically acceptable excipient, at least one 2-tolyl-4-alkylmorpholine derivative selected from the group consisting of 2-p-tolyl-4-isopropylmorpholine, 2-m-tolyl-4-methylmorpholine, 2-p-tolyl-4-methylmorpholine, 2-o-tolyl-4-tert.-butylmorpholine, 2-p-tolyl-4-tert.-butylmorpholine, 2-(m-trifluoromethylphenyl)-4-ethylmorpholine and their addition salts as the active principle.

Of course, in a composition of this type, the active principle, which is selected from the group consisting of the compounds according to the invention and their non-toxic salts, is present in a pharmaceutically effective quantity.

The compounds according to the invention possess the common property of acting as sedatives.

In general terms, CRL 40 875 (Example 1), CRL 40 912 (Example 2) and CRL 40 897 (Example 3) have sedative effects (hypomotility, hypothermia, reduction of intergroup aggressiveness and stimulant effects, especially of the α-adrenergic type. Briefly, they behave as sedatives at weak doses and as antidepressants at strong doses. They differ from their analog described in No. EP-A-80,940, namely CRL 40 915 (CP-1), by the variation in their sedative effects. More precisely, it has been found that the sedative effects of CRL 40 875, CRL 40 912 and CRL 40 897 increase continuously with the dose administered, up to a maximum value, and then decrease continuously and progressively as the dose increases, when the stimulant effects appear, and that, on the other hand, the sedative effects of CRL 40 915 do not appear continuously or progressively when the dose administered increases (cf., in this connection, No. EP-A-80,940 mentioned above, page 13, lines 6–10) but occur wholly or not at all: "no sedation at a given dose, significant sedation at the next highest dose used".

CRL 40 903 (Example 4), CRL 40 910 (Example 5) and CRL 41 092 (Example 6) have sedative effects and are particularly interesting as vasodilators, having regard to their cardiovascular properties.

Further advantages and characteristics of the invention will be understood more clearly on reading the following description of preparative examples and results of pharmacological tests; these data as a whole do not imply a limitation but are given by way of illustration.

PREPARATION I

Preparation of 2-p-tolyl-4-isopropylmorpholine hydrochloride (Example 1; Code no.: CRL 40 875)

100 g (0.469 mol) of p-methylphenacyl bromide are run dropwise into a solution consisting of 193.23 g (1.876 mol) of 2-isopropylaminoethanol and 500 ml of methanol. The mixture is heated under reflux for 3 hours and evaporated to dryness, the evaporation residue is taken up with 500 ml of water, extraction is carried out with ethyl acetate, the ethyl acetate phase is washed with water, dried over $MgSO_4$ and filtered to remove the $MgSO_4$, and the filtrate is evaporated to dryness.

The evaporation residue thus obtained, which contains N-β-hydroxyethyl-N-(4-methylphenacyl)isopropylamine, is taken up with 1500 ml of methanol. The mixture is cooled to −5° C. and 38 g (1 mol) of $NaBH_4$ are added. The reactants are left in contact for 8–12 hours at −5° C., 60 ml of acetic acid are then added, the mixture is evaporated to dryness, the evaporation residue is taken up with water, the pH is adjusted to 11 with NaOH, extraction is carried out with ethyl acetate, the ethyl acetate phase is washed with water and the said ethyl acetate phase is then extracted with a mixture of 250 ml of water and 50 ml of concentrated hydrochloric acid (d =1.19). The resulting aqueous phase is washed with diethyl ether, NaOH is added to pH 11, extraction is carried out with ethyl acetate, the ethyl acetate phase thus obtained is washed with water, dried over $MgSO_4$ and filtered, and the filtrate is then evaporated to dryness.

The evaporation residue thus obtained, which contains 2-(N-β-hydroxyethyl-N-isopropyl)amino-1-p-tolyl-ethanol, is run into 76 ml of sulfuric acid (d =1.84), the reaction medium being cooled by means of an ice bath. When the addition has ended, the reactants are left in contact at 5°–20° C. for 1 hour and the reaction medium is then poured into a mixture of 500 ml of water, ice and 274 ml of 10 N NaOH. Extraction is carried out with ethyl acetate and the ethyl acetate phase is washed with water, dried over $MgSO_4$ and filtered. The expected hydrochloride is precipitated from the filtrate by means of a solution of hydrogen chloride in ethanol. Recrystallization from an acetone/ethanol mixture (1:1 v/v) gives 38.7 g (overall yield: 32%) of CRL 40 875. Melting point =225° C. (with decomposition).

Analysis { % Cl measured = 14.08%
% Cl theoretical = 13.89%

PREPARATION II

Preparation of 2-m-tolyl-4-methylmorpholine hydrochloride (Example 2; Code no.: CRL 40 912)

67 g (0.5 mol) of metamethylacetophenone are dissolved in 100 ml of acetic acid. The solution is cooled in an ice bath and 25.8 ml of bromine are run in. The reactants are left in contact for one hour and the mixture is evaporated to dryness.

The evaporation residue thus obtained, which contains m-methylphenacyl bromide, is taken up with acetone and this solution is run into a solution of 2.5 mol (187.5 g) of 2-methylaminoethanol in 500 ml of methanol. The mixture is heated under reflux for 4 hours and evaporated to dryness, the evaporation residue is taken up with water and extraction is carried out with ethyl acetate. The organic phase is washed with water and extracted with a mixture of 500 ml of water and 60 ml of concentrated HCl (d = 1.19), the aqueous phase is washed with ethyl acetate, neutralized to pH = 11 with K$_2$CO$_3$ and extracted with ethyl acetate, the ethyl acetate phase is washed with water and the solvent is dried. The solution is evaporated to dryness.

The evaporation residue thus obtained, which contains N-β-hydroxyethyl-N-(3-methylphenacyl)methylamine, is taken up with 500 ml of methanol. 38 g (1 mol) of sodium borohydride are added. The reactants are left in contact overnight. The excess sodium borohydride is destroyed with 60 ml of acetic acid, the mixture is evaporated to dryness, the evaporation residue is taken up with water, extraction is carried out with ethyl acetate and the solvent is washed and dried with MgSO$_4$. The mixture is filtered and the filtrate is evaporated to dryness.

The evaporation residue thus obtained, which contains 2-(N-β-hydroxyethyl-N-methyl)amino-1-(m-tolyl)-ethanol, is run into 125 ml of concentrated sulfuric acid (d = 1.84), the reaction medium being cooled by means of an ice bath. The reactants are left in contact for one hour and the reaction mixture is introduced all at once into a mixture of 500 ml of water, ice and 460 ml of 10 N NaOH. Extraction is carried out with ether, the ether is washed with water and dried over MgSO$_4$ and the expected hydrochloride is then precipitated by means of a solution of hydrogen chloride in ethanol. Recrystallization from an acetone/ethanol mixture (1:1 v/v) gives 20 g (overall yield: 18%) of CRL 40 912. Melting point = 159° C.

Analysis { % Cl$^-$ measured = 15.77%
% Cl$^-$ theoretical = 15.60%

PREPARATION III

Preparation of 2-p-tolyl-4-methylmorpholine hydrochloride (Example 3; Code no.: CRL 40 897)

By following the procedure indicated in Preparation I, but replacing the N-β-hydroxyethylisopropylamine with N-β-hydroxyethylmethylamine, CRL 40 897 is obtained (with an overall yield of 23%). Melting point = 186° C.

Analysis { % Cl$^-$ measured = 16.16%
% Cl$^-$ theoretical = 15.60%

PREPARATION IV

Preparation of 2-p-tolyl-4-tert.-butylmorpholine hydrochloride (Example 4; Code no.: CRL 40 903)

A solution of 36.64 g (0.172 mol) of p-methyl-phenacyl bromide in acetone is run dropwise into a solution of 80.4 g (0.887 mol) of 2-tert.-butylaminoethanol in methanol. The mixture is heated under reflux for 4 hours and evaporated to dryness, the evaporation residue is taken up with water, extraction is carried out with ethyl acetate, the solvent is washed with water and extracted with 200 ml of water containing 20 ml of concentrated hydrochloric acid, the aqueous phase is washed with ethyl acetate and neutralized with sodium hydroxide solution, a further extraction is carried out with ethyl acetate, the ethyl acetate phase is washed with water, the solvent is dried over magnesium sulfate and the mixture is evaporated to dryness.

The dry product obtained is taken up in 500 ml of anhydrous methanol, and 10 g of sodium borohydride are added. The reactants are left in contact for several hours in order to effect the reduction reaction; 20 ml of acetic acid are subsequently added, the mixture is then evaporated to dryness, extraction is carried out with ethyl acetate and the solvent is washed with water and dried over magnesium sulfate. The mixture is then evaporated to dryness. The evaporation residue thus obtained is then run into 50 ml of concentrated sulfuric acid so as to effect the cyclization. The resulting mixture is left to stand for one hour and poured into a mixture containing 500 ml of water, 250 ml of 10 N sodium hydroxide solution and ice.

The mixture thus obtained is extracted with ether and the ether phase is washed with water and dried over magnesium sulfate. The expected hydrochloride is precipitated by the addition of a solution of hydrogen chloride in ethanol and purified by recrystallization from an ether/ethanol mixture (1:1 v/v). This gives 10 g of CRL 40 903. Melting point = 228° C.

Analysis { % Cl$^-$ measured = 13.32%
% Cl$^-$ theoretical = 13.17%

PREPARATION V

Preparation of 2-(m-trifluoromethylphenyl)-2-hydroxy-4-ethylmorpholine hydrochloride (Example 6; Code no.: CRL 41 092)

38 g (0.19 mol) of metatrifluoromethylacetophenone are dissolved in 300 ml of ether, and 30.64 g (0.19 mol) of bromine are run in dropwise. The reaction is left to proceed for about 1 hour, the mixture is evaporated to dryness and the evaporation residue is left in a vacuum desiccator, in the presence of KOH, in order to complete the drying. The residue thus obtained is taken up in 300 ml of ether and the resulting solution is run into a solution of 34.08 g (0.38 mol) of 2-ethylaminoethanol in 400 ml of ether. The reaction is left to proceed for 24 hours, with stirring. The following operations are then carried out: filtration of the insoluble material, washing with ether, washing with water, extraction of the ether phase with 200 ml of water containing 25 ml of concentrated hydrochloric acid, washing of the aqueous phase with ether, neutralization to pH 11 with sodium hydroxide solution and extraction with ether, the ether being washed with water and dried. The expected hydrochloride is precipitated by the addition of a solution of hydrogen chloride in ethanol. Recrystallization from an acetone/ethanol mixture (1:1 v/v) gives 23 g of CRL 41 092. Melting point = 194° C.

Analysis { % Cl$^-$ measured: 11.90%
% Cl$^-$ theoretical: 11.40%

The results of the tests which were undertaken have been summarized below.

TESTS RELATING TO CRL 40 875 (EXAMPLE 1)

A. CARDIOVASCULAR STUDY

The results of the cardiovascular tests demonstrated that CRL 40 875 is a hypotensive and tachycardiac agent in dogs. In normally hypertensive rats, CRL 40 875 does not modify the cardiovascular parameters.

B. NEUROPSYCHOPHARMACOLOGICAL STUDY

In the following tests, CRL 40 875, in solution in distilled water, was administered intraperitoneally in a volume of 20 ml/kg to male mice and 5 ml/kg to male rats.

I—PRETOXICITY

It is found on groups of three mice that CRL 40 875 causes thick saliva and convulsions, followed by death (of the 3 animals in the group) in 10 minutes, at a dose of 128 mg/kg and abdominal cramp and trembling, but no mortality, at doses of 64 mg/kg and 32 mg/kg. The LD-0 (maximum non-lethal dose) is therefore greater than 64 mg/kg, administered intraperitoneally, and less than 128 mg/kg, administered intraperitoneally, in male mice.

II—OVERALL BEHAVIOR AND REACTIVITIES

Groups of three mice are observed before and then 15 minutes, 30 minutes, 1 hour, 2 hours, 3 hours and 24 hours after the administration of CRL 40 875. It is found that:

a dose of 32 mg/kg causes:
  hypothermia (-4.1° C.) for 2 to 3 hours,
  a reduction in the reactivity to touch and muscular tonus for 2 hours,
  piloerection (2 out of 3 animals) for 2 to 3 hours, and moderate mydriasis for 0.5 hour;
a dose of 8 mg/kg causes:
  hypothermia ($-3.9°$ C.) for 1 hour, and
  piloerection (2/3) for 3 hours; and
a dose of 2 mg/kg causes:
  moderate hypothermia ($-1.5°$ C.) for 0.5 hour.

III—INTERACTION WITH APOMORPHINE (1°)—in mice

Groups of 6 mice receive CRL 40 875 0.5 hour before the subcutaneous injection of 1 or 16 mg/kg of apomorphine.

It is found that CRL 40 875 exerts an intrinsic hypothermic effect and, at a strong dose (32 mg/kg), partially opposes the hypothermia induced by 16 mg/kg of apomorphine, and that it does not modify the righting behavior and the stereotypies.

(2°)—in rats

CRL 40 875 is administered to groups of 6 rats 0.5 hour before the subcutaneous injection of 0.5 mg/kg of apomorphine.

It is found that CRL does not substantially impair the stereotype behavior induced by apomorphine in rats.

IV—INTERACTION WITH AMPHETAMINE

Amphetamine (2 mg/kg) is injected intraperitoneally into groups of 6 rats half an hour after the administration of CRL 40 875; it is observed that the stereotypies induced by amphetamine are not modified by CRL 40 875.

V—INTERACTION WITH RESERPINE

Four hours after the intraperitoneal injection of 2.5 mg/kg of reserpine, groups of 6 mice receive CRL 40 875. The effects on the temperature and ptosis are observed. It is observed that, at a strong dose, CRL 40 875 aggravates the hypothermia induced by reserpine, without modifying the ptosis induced by reserpine.

VI—INTERACTION WITH OXOTREMORINE

CRL 40 875 is administered to groups of 6 mice half an hour before the intraperitoneal injection of 0.5 mg/kg of oxotremorine.

(1°)—Action on the temperature

CRL 40 875 exerts a hypothermic effect and, at a strong dose, partially opposes the temperature drop caused by oxotremorine.

(2°)—Action on the trembling

At doses of 8 and 32 mg/kg, CRL 40 875 seems to increase the duration of the trembling due to oxotremorine.

(3°)—Action of the peripheral cholinergic symptoms

At doses of 0.5 mg/kg, 2 mg/kg, 8 mg/kg and 32 mg/kg, CRL 40 875 increases the proportion of mice which exhibit defecation following the administration of oxotremorine.

VII—ACTION ON THE FOUR PLATE TEST, TRACTION AND ELECTRIC SHOCK

The test is performed on groups of 10 mice half an hour after the administration of CRL 40 875.

It is observed that CRL 40 875 does not cause an increase in the number of punished passes, that it does not cause major motor incapacity and that it does not modify the convulsant effects of electric shock.

VIII—ACTION ON THE SPONTANEOUS MOTILITY

Half an hour after they have received CRL 40 875, the mice (6 per dose, 12 control animals) are placed in an actimeter, where their motility is recorded for 30 minutes.

It is found that, as from a dose of 2 mg/kg, CRL 40 875 causes hypomotility, which becomes very significant at doses of 8 and 32 mg/kg.

IX—ACTION ON THE INTERGROUP AGGRESSIVENESS

After they have stayed for 3 weeks in the two halves of a cage divided by an opaque partition, groups of 3 mice receive CRL 40 875. Half an hour later, the two groups from the same cage are brought together by removal of the partition, and the number of fights which occur in 10 minutes is noted.

It is found that, at the doses used (0.5 mg/kg and 2 mg/kg), which exert only a moderate effect on the motor activity, CRL 40 875 causes suppression of the fights.

X—ACTION TOWARDS SOME FORMS OF BEHAVIOR PERTURBED BY VARIOUS AGENTS (1°)—Motility reduced by habituation to the enclosure After they have stayed in the actimeters for 18 hours, the mice (6 per dose, 12 control animals) receive CRL 40 875. They are immediately returned to their respective enclosures and, half an hour later, their motility is recorded for 30 minutes.

It is observed that CRL 40 875 does not cause a resumption in the activity of mice accustomed to their enclosure.

(2°)—Motility reduced by hypoxic aggression

Half an hour after they have received CRL 40 875, the mice (10 per dose, 20 control animals) are subjected to acute hypobaric anoxia [pressure reduction of 600 mm Hg (i.e. about $8 \times 10^4$ pascals) in 90 seconds; release of vacuum in 45 seconds] and are then placed in an actimeter, where their motility is recorded for 10 minutes.

It is found that CRL 40 875 does not cause an improvement in the motor recovery in mice whose motility has been depressed following a brief period in a reduced-pressure enclosure.

(3°)—Asphyxiant anoxia

Groups of 20 mice receive CRL 40 875 half an hour before the intraperitoneal administration of 32 mg/kg of gallamine triiodoethylate (which is a reference curarizing agent).

It is observed that, at the doses used, CRL 40 875 delays the time taken for convulsions and death to occur following asphyxiant anoxia caused by a curarizing agent.

XI—CONCLUSION

The neuropsychopharmacological study of CRL 40 875 shows a number of sedative effects (hyporeactivity, hypothermia, hypomotility, significant reduction of aggressiveness, delayed onset of asphyxiant convulsions) at weak doses and antidepressant effects (antagonism of the hypothermia induced by apomorphine and oxotremorine) at strong doses. Furthermore, it is noted that CRL 40 875 exhibits signs of peripheral $\alpha$-adrenergic stimulation (salivation, piloerection, trembling).

TESTS RELATING TO CRL 40 897 (EXAMPLE 3)

NEUROPSYCHOPHARMACOLOGICAL STUDY

In the following tests, CRL 40 897, in solution in distilled water (pH 4), was administered intraperitoneally in a volume of 20 ml/kg to male mice and in a volume of 5 ml/kg to male rats, the procedures being those given above for CRL 40 875.

I—PRETOXICITY

On groups each containing three male mice, it is observed that CRL 40 897, administered intraperitoneally, causes dyspnea, copious salivation (for 1 out of 3 animals), convulsions ($\frac{2}{3}$) and death (3/3), which occurs in 10 minutes, at a dose of 256 mg/kg, dyspnea, trembling, convulsions ($\frac{2}{3}$) and sedation, but no mortality, at a dose of 128 mg/kg, and dyspnea, sedation and trembling ($\frac{1}{3}$) at a dose of 64 mg/kg. The LD-O is therefore greater than 128 mg/kg, administered intraperitoneally, and less than 256 mg/kg, administered intraperitoneally, in male mice.

II—OVERALL BEHAVIOR AND REACTIVITIES

It is found that CRL 40 897, studied on groups each containing three mice, causes:

at a dose of 64 mg/kg
  sedation (3 out of 3 animals) for 3 hours,
  depressed respiration (2/3) for 3 hours,
  significant salivation (3/3) for 1 hour,
  hypothermia ($-2.2°$ C.) for 1 to 2 hours, and
  mydriasis for 1 to 2 hours;
at a dose of 16 mg/kg
  hypothermia ($-2.4°$ C.) for 0.5 hour; and
at a dose of 4 mg/kg
  hypothermia ($-2.2°$ C.) for 0.5 hour.

III—INTERACTION WITH APOMORPHINE (1°) in mice

It is observed that, despite a hypothermic effect present as from 4 mg/kg, a high dose (64 mg/kg) of CRL 40 897 partially counteracts the temperature drop induced by apomorphine, without modifying the righting behavior and the stereotypies.

(2°) in rats

It is found that CRL 40 897 does not modify the stereotypies induced by apomorphine.

IV—INTERACTION WITH AMPHETAMINE

The control group of 6 rats has a low stereotypy index because of the total absence of reaction to amphetamine pick up in one of the six rats. The increase observed in the other groups merely reflect this anomaly.

V—INTERACTION WITH RESERPINE

It is observed that CRL 40 897 does not modify the hypothermia and ptosis induced by reserpine.

VI—INTERACTION WITH OXOTREMORINE (1°) Action on the temperature

It is observed that, despite a distinct hypothermic effect as from 4 mg/kg, a high dose (64 mg/kg) of CRL 40 897 partially counteracts the temperature drop induced by oxotremorine.

(2°)—Action on the trembling

It is found that the trembling due to oxotremorine is not influenced by CRL 40 897.

(3°)—Action on the peripheral cholinergic symptoms

It is observed that CRL 40 897 leaves unchanged the signs of peripheral cholinergic stimulation induced by oxotremorine.

VII—ACTION ON THE FOUR PLATE TEST, TRACTION AND ELECTRIC SHOCK

It is observed that CRL 40 897 does not cause an increase in the number of punished passes, that it does not cause major motor incapacity and that it does not modify the convulsant and lethal effects of electric shock.

VIII—ACTION ON THE SPONTANEOUS MOTILITY

It is noted that, as from a dose of 4 mg/kg, CRL 40 897 depresses the spontaneous motor activity of mice.

IX—ACTION ON THE INTERGROUP AGGRESSIVENESS

It is found that CRL 40 897 does not cause a distinct reduction in the number of fights.

X—ACTION TOWARDS SOME FORMS OF BEHAVIOR PERTURBED BY VARIOUS AGENTS (1°)—Motility reduced by habituation to the enclosure CRL 40 897 does not cause a resumption in the activity of mice accustomed to their enclosure.

(2°)—Motility reduced by hypoxic aggression

It is observed that CRL 40 897 does not cause any improvement in the motor recovery in mice whose motility has been depressed following a brief period in a reduced-pressure enclosure.

(3°)—Asphyxiant anoxia

It is found that, at the doses studied, CRL 40 897 delays the time taken for convulsions and death to occur following asphyxiant anoxia caused by a reference curarizing agent (gallamine triiodoethylate).

TESTS RELATING TO CRL 40 912 (EXAMPLE 2)

A. CARDIOVASCULAR STUDY

In anesthetized dogs, it is found that CRL 40 912, administered intraperitoneally, is a hypertensive agent at a dose of 1 mg/kg, that this effect decreases at a dose of 5 mg/kg and that bradycardia is caused as from 5 mg/kg.

In wake rats, it is noted that CRL 40 912 has no action on the mean blood pressure and that the bradycardia is of short duration.

Furthermore, it is found that CRL 40 912 has an effect of the $\alpha$-stimulant type.

B. NEUROPSYCHOPHARMACOLOGICAL STUDY

In the tests undertaken, CRL 40 912, in solution in distilled water (pH 4.5), was administered intraperitoneally in a volume of 20 ml/kg to male mice and in a volume of 5 ml/kg to male rats, the procedures being those given above for CRL 40 875.

It is found that;

the LD-O in male mice is greater than 128 mg/kg and less than 256 mg/kg, administered intraperitoneally;

CRL 40 912 has a very distinct peripheral α-adrenergic stimulant action (piloerection, exophthalmos, significant antagonism of the ptosis induced by reserpine);

on the other hand, at the central level, CRL 40 912 has sedative effects (hypomotility, hypothermia) comparable to those of α-adrenergic blocking substances or to clonidine (which is a stimulant of α-presynaptic receptors); these sedative effects take account of the reduction of aggressiveness and the delay in the time taken for convulsions and death to occur after asphxiant anoxia;

however, CRL 40 912 does not reduce the intensity of the stereotypies induced by amphetamine (as distinct from α-blockers and clonidine) and does not cause a resumption in the motor activity of mice accustomed to their enclosure (as distinct from clonidine); and finally, at a strong dose, CRL 40 912 opposes the hypothermic effects of apomorphine and oxotremorine and, at a weaker dose, opposes those of reserpine (as distinct from α-blockers and clonidine).

Briefly, CRL 40 912 acts as a sedative at a weak dose and then as an antidepressant at a strong dose, but the mechanism of its action in the organism is sometimes different from that of α-blockers and clonidine.

TESTS RELATING TO CRL 40 903 (EXAMPLE 4), CRL 40 910 (EXAMPLE 5) AND CRL 40 092 (EXAMPLE 6)

The toxicological and neuropsychopharmacological studies undertaken in accordance with the procedures described above for CRL 40 875 enabled the following observations to be made:

CRL 40 903:

the LD-O is greater than 128 mg/kg, administered intraperitoneally to male mice, doses of 64 mg/kg and 128 mg/kg, administered intraperitoneally to male mice, and of 32 mg/kg administered intraperitoneally to male rats, induce sedation and depressed respiration;

CRL 40 910:

the LD-O is greater than 128 mg/kg, administered intraperitoneally to male mice, a dose of 64 mg/kg, administered intraperitoneally to male mice, produces sedation (0.5 to 3 hours), depressed respiration (0.5 to 3 hours) and moderate hypothermia (0.5 hour);

CRL 41 092:

the LD-O is greater than 256 mg/kg, administered intraperitoneally to male mice, administered intraperitoneally to mice, a dose of 32 mg/kg causes moderate hypothermia and a dose of 128 mg/kg causes sedation (for 0.5 hour) and a reduction in the fear reaction, the reactivity to touch and the muscular tonus, and when administered intraperitoneally to rats, a dose of 64 mg/kg causes transistory sedation with a reduction in the reactivity to touch and the muscular tonus.

The results relating to the tests on the cardiovascular system have been summarized below.

CRL 40 903

When studied by intraduodenal administration and then intravenous administration to anesthetized dogs, CRL 40 903 has no action on the blood pressure; it has a tachycardiac effect as from 1 mg/kg; it increases the femoral flow rate as from 2.5 mg/kg (maximum +150% at 20 mg/kg); the vasodilation which it induces is not completely suppressed by propanolol; it does not modify the hypertension induced by noradrenaline and it reduces the hypotension induced by isoprenaline.

CRL 40 910

When administered intraduodenally to anesthetized dogs, CRL 40 910 significantly increases the femoral and vertebral flow rates at very weak doses (0.5 mg/kg); tachycardia appears at 1 mg/kg but remains weak; CRL 40 910 stimulates respiration in dogs; the rectal and skin temperatures increase progressively, as does the venous pressure; CRL 40 910 does not modify the effects of isoprenaline and it reduces the hypertension induced by noradrenaline; the effects of CRL 40 910 on the heart beat and the vertebral flow rate are antagonized by propanolol at a dose of 1 mg/kg administered intravenously, but the increase in the femoral flow rate caused by CRL 40 910 is not totally inhibited by propanolol.

CRL 41 092

When administered intraduodenally to anesthetized dogs, CRL 41 092 greatly increases the femoral flow rate as from 1 mg/kg; a reduction in the vertebral flow rate and also in the rectal and skin temperatures is observed; CRL 41 092 does not modify the heart beat and it tends to increase the blood pressure; CRL 41 092 is very slightly $\beta_1-$ and $\beta_2-$; it increases the hypertension induced by noradrenaline; propanolol, injected into dogs at the end of the test, very slightly reduces the heart beat and femoral flow rate due to CRL 41 092, the femoral flow rate nevertheless remaining above its control value.

In clinical trials, good results were obtained on man with CRL 40 875 (Example 1), CRL 40 912 (Example 2) and CRL 40 897 (Example 3) in the treatment of depressions.

TABLE I

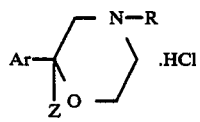

| PRODUCT | CODE No. | Ar | R | Z | Melting point (inst.) |
|---|---|---|---|---|---|
| Example 1 | CRL 40 875 | p-tolyl | $CH(CH_3)_2$ | H | 225° C. (a) |
| Example 2 | CRL 40 912 | m-tolyl | $CH_3$ | H | 159° C. |
| Example 3 | CRL 40 897 | p-tolyl | $CH_3$ | H | 186° C. |
| Example 4 | CRL 40 903 | p-tolyl | $C(CH_3)_3$ | H | 228° C. |
| Example 5 | CRL 40 910 | o-tolyl | $C(CH_3)_3$ | H | 230° C. |

TABLE I-continued

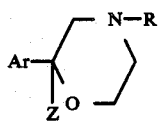

| PRODUCT | CODE No. | Ar | R | Z | Melting point (inst.) |
| --- | --- | --- | --- | --- | --- |
| Example 6 | CRL 41 092 | m-(CH$_3$)—C$_6$H$_4$ | CH$_2$CH$_3$ | OH | 194° C. |
| CP-1 (b) | CRL 40 915 | o-tolyl | CH$_3$ | H | 192° C. (a) |

Notes
(a): with decomposition
(b): comparison product described in EP-A-80,940.

What is claimed is:

1. A 2-tolylmorpholine derivative corresponding to the general formula $$\text{Ar} \underset{Z}{\overset{}{\diagdown}} \underset{O}{\overset{N-R}{\diagup}} \quad (I)$$

(in which Ar is a tolyl group, Z is H and R is a C$_1$-C$_4$ alkyl group), which is selected from the group of 2-tolyl-4-alkylmorpholines consisting of
   (a) 2-p-tolyl-4-isopropylmorpholine and its addition salts,
   (b) 2-m-tolyl-4-methylmorpholine and its addition salts,
   (c) 2-p-tolyl-4-methylmorpholine and its addition salts,
   (d) 2-o-tolyl-4-tert.-butylmorpholine and its addition salts,
   (e) 2-p-tolyl-4-tert.-butylmorpholine and its addition salts.

2. A tolymorpholine derivative according to claim 1 which is 2-p-tolyl-4-methylmorpholine and its addition salts.

3. A tolylmorpholine derivative according to claim 1 which is 2-m-tolyl-4-methylmorpholine and its addition salts.

4. A tolylmorpholine derivative according to claim 1 which is 2-p-tolyl-4-isopropylmorpholine and its addition salts.

5. A tolylmorpholine derivative according to claim 1 which is a 2-p-tolyl-4-tert.-butylmorpholine and its addition salts.

6. A tolylmorpholine derivative according to claim 1 which is a 2-o-tolyl-4-tert.-butylmorpholine and its addition salts.

7. A therapeutic composition which contains, in association with a physiologically acceptable excipient, at least one 2-tolyl-4-alkylmorpholine derivative selected from the group consisting of 2-p-tolyl-4-isopropylmorpholine, 2-m-tolyl-4-methylmorpholine, 2-p-tolyl-4-methylmorpholine, 2-o-tolyl-4-tert.-butylmorpholine, 2-p-tolyl-4-tert.-butylmorpholine and their addition salts.

* * * * *